United States Patent [19]

Engelhardt et al.

[11] Patent Number: 5,011,892
[45] Date of Patent: Apr. 30, 1991

[54] HYDROPHILIC SWELLABLE GRAFT COPOLYMERS, THEIR PREPARATION AND USE

[75] Inventors: Friedrich Engelhardt; Ulrich Riegel, both of Frankfurt am Main, Fed. Rep. of Germany

[73] Assignee: Cassella AG, Frankfurt am Main, Fed. Rep. of Germany

[21] Appl. No.: 498,722

[22] Filed: Mar. 26, 1990

[30] Foreign Application Priority Data

Apr. 7, 1989 [DE]  Fed. Rep. of Germany ....... 3911433

[51] Int. Cl.$^5$ .............................................. C08F 283/06
[52] U.S. Cl. ................................... 525/404; 528/271; 528/391; 528/393
[58] Field of Search ........................ 525/404; 526/209; 528/271, 391, 393

[56] References Cited

U.S. PATENT DOCUMENTS

| | | | |
|---|---|---|---|
| 3,963,805 | 6/1976 | Chu ..................................... | 525/404 |
| 3,990,459 | 11/1976 | Papantoniu ..................... | 525/404 X |
| 4,528,334 | 7/1985 | Knopf et al. ......................... | 525/404 |
| 4,705,525 | 11/1987 | Abel et al. ....................... | 525/404 X |

*Primary Examiner*—Earl Nielsen
*Attorney, Agent, or Firm*—Connolly and Hutz

[57] ABSTRACT

The present invention relates to hydrophilic, swellable graft copolymers composed, in random distribution, of 0.5 to 20% by weight of radicals of the general formula I

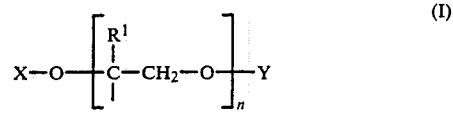

79 to 99% by weight of radicals containing an acidic group, of the general formula II

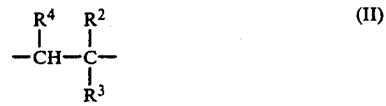

and 0.1 to 2% by weight of crosslinking structures which are derived from monomers having at least two olefinically unsaturated double bonds, where the radicals X, Y, $R^1$ to $R^4$ and n have the meanings given in claim 1, and which are used as absorbents for water and aqueous solutions.

14 Claims, No Drawings

HYDROPHILIC SWELLABLE GRAFT COPOLYMERS, THEIR PREPARATION AND USE

The present invention relates to hydrophilic, swellable graft copolymers composed, in random distribution, of 0.5 to 20% by weight of radicals of the general formula I

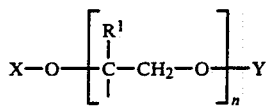

79 to 99% by weight of radicals containing an acidic group, of the general formula II

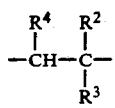

and 0.1 to 2% by weight of radicals of a crosslinking agent which are derived from monomers having at least two olefinically unsaturated double bonds, where X denotes $(C_1-C_{22})$-alkyl, aryl, aralkyl or Y, Y denotes $COCH_3$, $CH_2COOR^2$, $COCH_2CH_2COOH$,

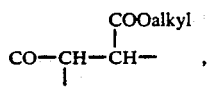

$COOR^2$, $CH_2COCH_2COOR^2$, $COOR^2$, $CH_2COCH_2COOR^2$,

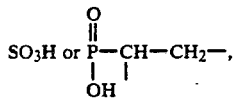

n denotes 2 to 300, $R^1$ denotes hydrogen or methyl, $R^2$ independently of one another denotes hydrogen, methyl or ethyl, $R^3$ denotes the carboxyl group, the sulphonyl group, the phosphonyl group, which optionally may be esterified with alkanol having 1 to 4 carbon atoms, or denotes a group of the formula

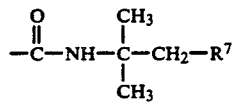

in which $R^7$ represents the sulphonyl group or the phosphonyl group, $R^4$ denotes hydrogen, methyl, ethyl or the carboxyl group, and also to their preparation and use as absorbents for water and aqueous solutions, for example in sanitary items, for soil improvement or as filtration auxiliaries.

Swellable polymers which absorb aqueous solutions are used for the preparation of tampons, diapers, sanitary towels and other sanitary items and also as water-retaining agents in market gardening.

Known absorption resins of this type include crosslinked carboxymethylcellulose, partially crosslinked polyalkylene oxide, hydrolysates of starch-acrylonitrile graft copolymers or salts of partially crosslinked polyacrylic acid.

These known polymers all have disadvantages, in particular in the absorption of aqueous electrolyte solution and also blood and urine.

The prior art achieves high absorbencies with low gel stabilities in the swollen polymer particles. Tacky materials are formed which impair the absorbency of the products made from these polymers.

It is known that increasing the crosslinked density improves the gel stability and also the rate of liquid uptake but simultaneously reduces the absorption capacity. This measure is unhelpful in that the absorption capacity is the most important property of the polymer.

The object of the present invention is to provide modified polymers which absorb aqueous solutions, have a high absorption rate and, in the swollen state, thus for non-tacky hydrogel particles of high gel stability.

Surprisingly, it has now been found that the desired range of properties is achieved by the graft copolymers according to the invention since the macromolecular network of these polymers physically brings about an increase in the gel stability or gel strength of the swollen polymer and also an improved electrolyte tolerance.

Preference is given to products according to the invention composed of 0.5 to 15% by weight of radicals of the general formula I, 84 to 99% by weight of radicals of the general formula II and 0.1 to 1.8% by weight of crosslinking structures derived from monomers having at least two olefinically unsaturated double bonds.

Particular preference is given to products according to the invention composed of 1 to 10.5% by weight of radicals of the general formula I, 88 to 98.5% by weight of radicals of the general formula II and 0.3 to 1.5% by weight of crosslinking structures derived from monomers having at least two olefinically unsaturated double bonds.

In the graft copolymers according to the invention, the radicals of the general formula I may all have exactly the same structure, but they may also differ with regard to the radical $R^1$ and/or the number n. For instance, $R^1$ may at random be hydrogen or methyl but it is also possible to have sequences of relatively large polymer sections in which $R^1$ denotes in each case hydrogen only or methyl only.

If X represents aryl, this preferably has 3 to 8 carbon atoms and preferably denotes in particular phenyl, tert-butyl-phenyl or nonylphenyl. If X represents aralkyl, this preferably has 3 to 8 carbon atoms in the aryl radical and 1 to 22 carbon atoms in the alkyl radical.

If Y represents the radical

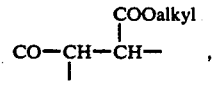

the said alkyl group preferably has 1 to 22 carbon atoms.

Y preferably denotes $COCH_3$, $CH_2COOR^2$, $COCH_2CH_2COOH$, $COOR^2$, $CH_2COCH_2COOR_2$ and

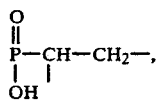

$R^2$ in the radicals of the general formula II preferably denotes hydrogen or methyl. $R^3$ preferably represents the carboxyl group, the sulphonyl group or the phosphonyl group. Particular preference is given to the carboxyl group. $R^4$ preferably denotes hydrogen.

The abovementioned crosslinking structures may be derived from any suitable monomers having at least two olefinically unsaturated double bonds.

Examples of suitable monomers are compounds having at least two alkenyl groups, for example vinyl or alkyl, or at least two alkenoyl groups, for example acrylate or methacrylate.

Preference is given to the crosslinking structures derived from monomers containing 2, 3 or 4 ethylenically unsaturated double bonds.

Particular preference is given to the crosslinking structures derived from trimethylolpropane triacrylate, tetraallyloxyethane or methylenebisacrylamide.

Other crosslinking structures can be obtained by adding polyfunctional epoxides such as, for example, ethylene glycol diglycidyl ether or a cycloaliphatic diepoxide.

Most particular preference is given to graft copolymers according to the invention in which a plurality of the above-mentioned preferred or particularly preferred features are present.

The graft copolymers according to the invention can be prepared by known polymerization processes. Preference is given to the polymerization in aqueous solution by the process known as gel polymerization. In this process, 15–50% strength aqueous solutions of the comonomers are polymerized with known suitable catalyst systems without mechanical agitation using the Trommsdorff-Norrish effect (Bios Final Rep. 363.22; Makromol. Chem. 1, 169 (1947)).

The polymerization reaction can be carried out in the temperature range between 0° C. and 130° C., preferably between 10° C. and 100° C., either at atmospheric pressure or under elevated pressure. As usual, the polymerization can also be carried out in an inert gas atmosphere, preferably under nitrogen.

The polymerization can be initiated by high-energy electromagnetic radiation or by the usual chemical polymerization initiators, for example organic peroxides, such as benzoyl peroxide, tert-butyl hydroperoxide, methyl ethyl ketone peroxide, cumene hydroperoxide, azo compounds such as azodiisobutyronitrile and also inorganic peroxide compounds such as $(NH_4)_2S_2O_8$ or $K_2S_2O_8$ or $H_2O^2$, optionally in combination with reducing agents such as sodium hydrogen sulphite, and iron-(II) sulphate or redox systems which contain, as the reducing component, an aliphatic and aromatic sulphinic acid such as benzenesulphinic acid and toluenesulphinic acid or derivatives of these acids such as, for example, Mannich adducts of sulphinic acid, aldehydes and amino compounds, as described in DE-C-1,301,516. As a rule, for every 100 g of total monomers, 0.03 to 2 g of polymerization initiator are used.

Post-heating of the polymer gels for several hours in the temperature range 50°–130° C., preferably 70°–100° C., further improves the qualities of the polymers.

The copolymers according to the invention which have been prepared by this method and are present in the form of aqueous jellies can be obtained in solid form by mechanical comminution using suitable equipment followed by conventional drying processes and be used in this form.

Graft copolymers according to the invention are consequently advantageously obtained if 0.5 to 20% by weight, preferably 0.5 to 15, in particular 1 to 10.5, % by weight of a polyalkylene oxide compound of the general formula Ia

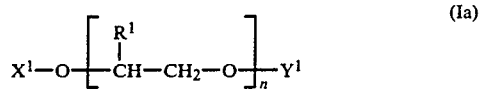

or optionally an alkali metal salt, ammonium salt or amine salt thereof, 79 to 99% by weight, preferably 84 to 99, in particular 88 to 98.5, % by weight of an unsaturated acid of the general formula IIa

or an alkali metal salt, ammonium salt or amine salt thereof and 0.1 to 2% by weight, preferably 0.1 to 1.8, in particular 0.3 to 1.5, % by weight of a monomer having at least two olefinically unsaturated double bonds, where $X^1$ denotes $(C_1-C_{22})$-alkyl, aryl, aralkyl or Y,
$Y^1$ denotes $COCH_3$, $CH_2COOR^2$, $COCH_2CH_2COOH$, $CO-CH=CH-COOalkyl$, $COOR^2$, $CH_2COCH_2COOR^2$, $CO-CH=CH_2$, $SO_3H$ or

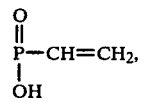

and the radicals $R^1$ to $R^4$ and the number n have the meanings given above, are reacted under the conditions of gel polymerization.

The polyalkylene oxide compounds of the general formula Ia can be obtained by known reactions of compounds with reactive groups such as anhydrides, acid chlorides, halocarboxylic acids or esters thereof or halosulphonic acids with polyalkylene oxides.

Preferred polyalkylene oxides are polypropylene oxide and polyethylene oxide, copolymers or block copolymers of ethylene oxide and propylene oxide, oxyethylates, oxypropylates or oxyethyloxypropylates of aliphatic $C_1$ to $C_{22}$ alkyl alcohols, phenol, tert-butylphenol or nonylphenol.

Preferred reactants for terminating the polymer chain are chloroacetic acid and esters thereof, chloroformic acid and esters thereof, the monochloride of vinylphosphonic acid and the dichloride of vinylphosphonic acid, succinic anhydride, acetic anhydride, and monochloroacetic acid.

The monomers of the formula IIa are known compounds such as for example acrylic acid, methacrylic acid, vinylsulphonic acid, maleic acid, fumaric acid, crotonic acid, 2-acrylamido-2-methylpropanesulphonic acid, 2-acrylamido-2-methylpropane-phosphonic acid and vinylphosphonic acid, and also the half-esters thereof.

The polyolefinic monomers used as crosslinking agents are commercial products. Examples are bisacrylamidoacetic acid, trimethylolpropane triacrylate, tetraallyloxyethane, and methylenebisacrylamide.

The graft copolymers according to the invention are eminently suitable as absorbents for water and aqueous solutions, so that they can be used advantageously as water-retaining agents in market gardening, as filtration auxiliaries and particularly as absorbent components in sanitary items such as diapers, tampons or sanitary towels.

The following Examples 1 to 13 illustrate the preparation of graft copolymers according to the invention.

EXAMPLE 1

A polyethylene bucket well insulated with expanded plastic material and with a capacity of 10 liters is initially charged with 4920 g of deionized water and then 1493 g of sodium bicarbonate are dispersed in the water and 1910 g of acrylic acid slowly metered in such that excessive foaming of the reaction solution is avoided, this solution being cooled to a temperature of about 12°–10° C. Then 40 g of the reaction product according to Example a (see below) serving as the graft base, 20 g of trimethylolpropane triacrylate dissolved in 20 g of a polyglycol ether based on a synthetic $C_{12}$–$C_{15}$-oxoalcohol with 13 ethylene oxide units, 10 g of sodium diisooctylsulphosuccinate (REWOPOL V 2133 supplied by REWO, Steinau) and 30 g of a cycloaliphatic epoxide (DIEPOXID supplied by DEGUSSA AG) are added. At a temperature of 10°–12° C., the initiators, a redox system consisting of 2.2 g of 2,2'-azobisamidinopropane dihydrochloride dissolved in 20 g of water, 4.4 g of potassium peroxydisulphate dissolved in 170 g of water and 6 g of sodium pyrosulphite dissolved in 120 g of water are added in succession with thorough stirring. The reaction solution is then left to stand without stirring and the polymerization which commences, and during which the temperature rises to about 85° C., results in a solid gel. This is then mechanically comminuted, dried at temperatures above 80° C. and ground.

The product described above was incorporated by conventional methods into a baby's diaper and gave particularly good liquid retention properties. Preparation of the graft bases:

EXAMPLE A 20.0 g of succinic anhydride are added at room temperature with stirring to 312 g of a block copolymer composed of 1.03 mol of propylene oxide and 0.91 mol of ethylene oxide with a hydroxyl number of 36 and this mixture is heated with stirring to 80° C. During this procedure, the succinic anhydride dissolves in a weakly exothermic reaction and a clear colourless solution is formed.

EXAMPLE B

A four-necked flask with an azeotropic distillation attachment and nitrogen feed is charged with 1010 g (0.495 mol) of polypropylene glycol 2020 dissolved in 500 ml of toluene, and dehydrated, i.e. azeotropically distilled for 3 h, during which 43 g of water are separated off. At 105°–110° C., in the course of 30 min, 112.5 g (1.1 mol) of acetic anhydride are added dropwise and the mixture is then stirred for 2 h at 105°–110° C. Toluene, acetic acid and excess acetic anhydride are distilled off under water pump vacuum. The residue is 1020 g of a colourless oil.

EXAMPLE C 4621 g (1.0 mol) of a polyglycol ether based on nonylphenol with 100 ethylene oxide units are melted. At 90°–100° C., 102 g (1.0 mol) of acetic anhydride are added dropwise, the mixture is stirred for 30 min and then the acetic acid formed is distilled off under water pump vacuum. A colourless solution is produced which solidifies at room temperature to form a solid wax.

EXAMPLE D

A reaction flask is charged with 345 g of a block copolymer composed of 1.6 mol of propylene oxide and 0.2 mol of ethylene oxide with a hydroxyl number of 65 which are dissolved in 350 ml of ethyl acetate, 40.5 g of triethylamine are added and 37.8 g of monochloroacetic acid are slowly added. Stirring is maintained for 1 h, the triethylamine hydrochloride is filtered off under suction and the solvent is distilled off under water pump vacuum. The residue is 368 g of a colourless oil.

EXAMPLE E

Reaction similar to (1a) but with a copolymer composed of 0.35 mol of propylene oxide and 1.82 mol of ethylene oxide with a hydroxyl number of 17.

EXAMPLE F

Reaction similar to (1a) but with a copolymer composed of 1.6 mol of propylene oxide and 0.2 mol of ethylene oxide with a hydroxyl number of 65.

EXAMPLE G

Reaction similar to (1d) but with nonylphenol oxyethylate having 30 ethylene units and ethyl chloroacetate.

EXAMPLE H

Reaction similar to (1d) but with nonylphenol oxyethylate having 30 ethylene units and chloroformic acid.

EXAMPLE I

Reaction similar to (1d) but with a copolymer composed of 1.03 mol of propylene oxide and 0.91 mol of ethylene oxide with a hydroxyl number of 36 and the monochloride of vinylphosphonic acid.

EXAMPLE K

Reaction similar to (1d) but with polypropylene glycol 2020 and monochloroacetic acid.

EXAMPLE L

Reaction similar to (1c) but with tert-butylphenol oxyethylate having 80 ethylene oxide units and acetic anhydride.

EXAMPLE M

Reaction similar to (1d) but with phenol oxyethylate having 15 propylene oxide units and the dichloride of vinylphosphonic acid.

EXAMPLE 2

A 10 liter plastic bucket is initially charged with 4419 g of ice and 1894 g of acrylic acid and then 1573 g of 50% strength NaOH solution are slowly metered in, followed by the addition of 100 g of the reaction product according to Example 1a serving as the graft base, 6 g of methylenebisacrylamide dispersed in 100 g of water, and 10 g of Rewopol V 2133. The reaction solution is brought to 20° C. and then the initiators, a redox system consisting of 6 g of potassium peroxydisulphate dissolved in 170 g of water, and 0.15 g of ascorbic acid dissolved in 120 g of water are added and the mixture is left to stand without stirring. The gel resulting from the polymerization is then mechanically comminuted, dried at temperatures above 80° C. and ground.

EXAMPLE 3

A 10 liter polyethylene bucket is initially charged with 5130 g of deionized water, 1888 g of acrylic acid and 50 g of the reaction product according to Example (1c) serving as the graft base. 12 g of tetraallyloxyethane and 10 g of REWOPOL V 2133 are stirred in. After bringing the reaction solution to 18°–20° C., the initiators, 6 g of potassium peroxydisulphate in 170 g of water and 0.2 g of ascorbic acid in 20 g of water are added in succession and the well insulated reaction vessel is left to stand without stirring. After the reaction has commenced, the temperature increases to about 90° C. and a solid gel is formed. This is mechanically comminuted using an extruder to which 1540 g of 50% strength NaOH are continuously metered in, the water being partially evaporated. The flaky polymer is then finally dried at temperatures above 80° C. and ground.

Other examples of the preparation of graft copolymers according to the invention in accordance with the Examples 1 and 2 described here are listed in the following table. The percentages given are percentages by weight relative to total proportion of monomers.

The following abbreviations are used:
AS: acrylic acid
MAS: methacrylic acid
CTS: crotonic acid
VPS: vinylphosphonic acid
VPE: half-ester of vinylphosphonic acid
AMP: 2-acrylamido-2-methylpropanesulphonic acid
AMPP: 2-acrylamido-2-methylpropanephosphonic acid
TMPTA: trimethylolpropane triacrylate
TAE: tetraallyloxyethane
MBA: methylenebisacrylamide

What is claimed is:
1. Hydrophilic, swellable graft copolymers composed, in random distribution, of 0.5 to 20% by weight of radicals of the general formula I

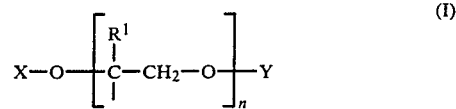

79 to 99% by weight of radicals containing at acidic group, of the general formula II

and 0.1 to 2% by weight of radicals of a crosslinking agent which are derived from monomers having at least two olefinically unsaturated double bonds, where X denotes $(C_1-C_{22})$-alkyl, aryl, aralkyl or Y
Y denotes $COCH_3$, $CH_2COOR^2$, $COCH_2CH_2COOH$,

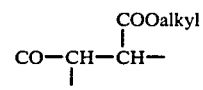

$COOR^2$, $CH_2COCH_2COOR^2$, $SO_3H$ or

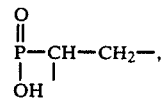

n denotes 2 to 300,
$R^1$ denotes hydrogen or methyl
$R^2$ independently of one another denotes hydrogen, methyl or ethyl
$R^3$ denotes the carboxyl group, the sulphonyl group, the phosphonyl group which optionally may be

| Example | Prepared as in Example | AS (%) | MAS (%) | AMP (%) | AMPP (%) | VPS (%) | VPE (%) | CTS (%) | Graft base as in Example | (%) | MBA (%) | TMPTA (%) | TAE (%) | Degree of neutralization (%) |
|---|---|---|---|---|---|---|---|---|---|---|---|---|---|---|
| 4 | 1 | 94.4 | | | | | | | 1e | 5 | | 0.6 | | 45 |
| 5 | 1 | 94.4 | | | | | | | 1f | 5 | | 0.6 | | 45 |
| 6 | 1 | 89.4 | | | | | | | 1g | 10 | | 0.6 | | 45 |
| 7 | 1 | 94.4 | | | | | | | 1h | 5 | | 0.6 | | 45 |
| 8 | 1 | 94.4 | | | | | | | 1i | 5 | | 0.6 | | 45 |
| 9 | 1 | 94.4 | | | | | | | 1k | 5 | | 0.6 | | 45 |
| 10 | 1 | 88.5 | | | | | | | 1l | 10 | | 1.5 | | 70 |
| 11 | 1 | 94.4 | | | | | | | 1m | 5 | | 0.6 | | 45 |
| 12 | 2 | 89.7 | | | | | | | 1c | 10 | 0.3 | | | 75 |
| 13 | 2 | 89.4 | | | | | | | 1c | 10 | | | 0.6 | 78 |
| 14 | 1 | 98.4 | | | | | | | 1c | 1 | | 0.6 | | 45 |
| 15 | 1 | 70.0 | 10.0 | 9.5 | | | | | 1c | 10 | | 0.5 | | 48 |
| 16 | 2 | 65.25 | | 25.0 | | 4.0 | | | 1c | 5 | 0.25 | | | 45 |
| 17 | 2 | 75.0 | 5.0 | 10.0 | | | 4.2 | | 1c | 5 | | 0.8 | | 60 |
| 18 | 2 | 85.0 | | 5.0 | 4.5 | | | | 1c | 5 | 0.5 | | | 70 |
| 19 | 1 | 72.4 | | 20.0 | | 4.2 | | | 1c | 3 | 0.4 | | | 80 |
| 20 | 1 | 81.0 | 10.0 | | | | 4.0 | | 1c | 4 | | 1.0 | | 36 |
| 21 | 2 | 90.0 | | | 4.6 | | | | 1c | 5 | | | 0.4 | 25 |
| 22 | 2 | 79.0 | | 19.0 | | | | | 1c | 1 | | 1.0 | | 40 |
| 23 | 1 | 72.0 | | 19.3 | | | | 5.0 | 1c | 3 | | 0.7 | | 48 |
| 24 | 1 | 90.0 | | | | 1.0 | | | 1c | 8 | | 1.0 | | 32 | esterified with alkanol having 1 to 4 carbon atoms, or denotes a group of the formula

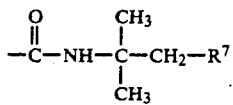

in which R⁷ represents the sulphonyl group or the phosphonyl group, and $R^4$ denotes hydrogen, methyl, ethyl or the carboxyl group.

2. Graft copolymers according to claim 1, characterized in that they are composed, in random distribution, of 1 to 10.5% by weight of radicals of the general formula I, 88 to 98.5% by weight of radicals of the general formula II and 0.3 to 1.5% by weight of crosslinking structures.

3. Graft copolymers according to claim 1, characterized in that the radicals of the general formula I differ with regard to the radical $R^1$ or the number n.

4. Graft copolymers according to claim 1, characterized in that $R^2$ in the radicals of the general formula II denotes hydrogen or methyl, $R^3$ denotes the carboxyl group, the sulphonyl group or the phosphonyl group and $R^4$ denotes hydrogen.

5. Graft copolymers according to claim 1, characterized in that $R^3$ in the radicals of the general formula II denotes the carboxyl group.

6. Graft copolymers according to claim 1, characterized in that the crosslinking structures are derived from monomers having at least two alkenyl groups or at least two alkenyol groups.

7. Graft copolymers according to claim 1, characterized in that the crosslinking structures are derived from trimethylolpropane triacrylate, tetraallyloxyethane or methylenebisacrylamide.

8. Process for the preparation of the graft copolymers claimed in claim 1, characterized in that 0.5 to 20% by weight of polyalkylene oxide compound of the general formula Ia

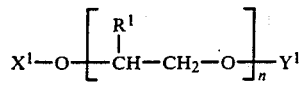

or optionally an alkali metal salt, ammonium salt or amine salt thereof, 79 to 99% by weight of an unsaturated acid of the general formula IIa

or an alkali metal salt, ammonium salt or amine salt thereof, and 0.1 to 2% by weight of a monomer having at least two olefinically unsaturated double bonds, where
$X^1$ denotes ($C_1$-$C_{22}$-alkyl, aryl, aralkyl or Y,
$Y^1$ denotes $COCH_3$, $CH_2COOR^2$, $COCH_2CH_2COOH$, $CO-CH=CH-COOalkyl$, $COOR^2$, $CH_2COCH_2COOR^2$, $CO-CH=CH_2$, $SO_3H$ or

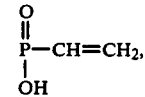

and $R^1$ to $R^4$ and n are as defined in claim 1, are reacted under the conditions of gel polymerization.

9. A process according to claim 8 wherein the amount of the polyalkylene oxide compound of the general formula Ia is 0.5 to 15% by weight.

10. A process according to claim 8 wherein the amount of the polyalkylene oxide compound of the general formula Ia is 1 to 10.5% by weight.

11. A process according to claim 8 wherein the amount an unsaturated acid of the general formula IIa is 84 to 99% by weight.

12. A process according to claim 8 wherein the amount an unsaturated acid of the general formula IIa is 88 to 98.5% by weight.

13. A process according to claim 8 wherein the amount of a monomer having at least two olefinically unsaturated double bonds is 0.1 to 1.8% by weight.

14. A process according to claim 8 wherein the amount of a monomer having at least two olefinically unsaturated double bonds is 0.3 to 1.5, % by weight.

* * * * *